(12) United States Patent
Seu-Salerno et al.

(10) Patent No.: US 8,226,961 B2
(45) Date of Patent: Jul. 24, 2012

(54) LOOSE POWDERS TURNING INTO LIQUIDS UNDER COSMETIC APPLICATION

(75) Inventors: Martine Seu-Salerno, Neuilly-sur-seine (FR); Laurence Fillardet, Pontoise (FR); Virginie Boulier, Condecourt (FR)

(73) Assignee: LCW, Sant-Ouen l'Aumone (FR)

( * ) Notice: Subject to any disclaimer, the term of this patent is extended or adjusted under 35 U.S.C. 154(b) by 810 days.

(21) Appl. No.: 10/527,948

(22) PCT Filed: Sep. 16, 2003

(86) PCT No.: PCT/FR03/02732

§ 371 (c)(1),
(2), (4) Date: Nov. 14, 2005

(87) PCT Pub. No.: WO2004/026277

PCT Pub. Date: Apr. 1, 2004

(65) Prior Publication Data

US 2006/0182772 A1    Aug. 17, 2006

(30) Foreign Application Priority Data

Sep. 17, 2002  (FR) .................................... 02 11515

(51) Int. Cl.
*A61K 8/11* (2006.01)
(52) U.S. Cl. ...................................................... 424/401
(58) Field of Classification Search .................. 424/401
See application file for complete search history.

(56) References Cited

U.S. PATENT DOCUMENTS

| 4,127,643 | A |   | 11/1978 | Carlin |   |
|---|---|---|---|---|---|
| 4,411,717 | A |   | 10/1983 | Anderson |   |
| 4,456,486 | A |   | 6/1984 | Bernhard |   |
| 4,572,739 | A |   | 2/1986 | Rasmussen |   |
| 5,023,065 | A | * | 6/1991 | Ohno et al. | 423/326 |
| 5,063,050 | A | * | 11/1991 | Verdon et al. | 424/63 |
| 5,167,708 | A |   | 12/1992 | Wilhelm et al. |   |
| 5,356,627 | A |   | 10/1994 | Da Cunha et al. |   |
| 5,458,976 | A |   | 10/1995 | Horino et al. |   |
| 5,482,547 | A |   | 1/1996 | Bugnon et al. |   |
| 5,496,544 | A | * | 3/1996 | Mellul et al. | 424/78.03 |
| 5,622,693 | A | * | 4/1997 | Funatsu | 424/69 |
| 5,645,903 | A | * | 7/1997 | Tanaka et al. | 428/34.1 |
| 6,315,990 | B1 |   | 11/2001 | Farer et al. |   |
| 6,335,390 | B1 |   | 1/2002 | Seeger et al. |   |
| 6,410,470 | B1 |   | 6/2002 | Wallar et al. |   |
| 6,413,548 | B1 |   | 7/2002 | Hamer et al. |   |
| 6,471,950 | B1 |   | 10/2002 | Farer et al. |   |
| 6,548,454 | B1 | * | 4/2003 | Yamamoto et al. | 508/138 |
| 6,576,248 | B1 |   | 6/2003 | Simard et al. |   |

| 2001/0036447 | A1 |   | 11/2001 | Farer et al. |   |
|---|---|---|---|---|---|
| 2002/0012682 | A1 | * | 1/2002 | Kashimoto | 424/401 |
| 2002/0034525 | A1 | * | 3/2002 | Sakai et al. | 424/401 |
| 2003/0202993 | A1 |   | 10/2003 | Sato et al. |   |
| 2004/0028710 | A1 | * | 2/2004 | Oka et al. | 424/401 |
| 2004/0156811 | A1 |   | 8/2004 | Lynch |   |
| 2006/0115438 | A1 |   | 6/2006 | Vonbehren et al. |   |
| 2006/0182698 | A1 |   | 8/2006 | Grizzo et al. |   |
| 2008/0038301 | A1 |   | 2/2008 | Ueda |   |
| 2008/0038302 | A1 |   | 2/2008 | Tanaka |   |

FOREIGN PATENT DOCUMENTS

| DE | 102005060679 | 6/2007 |
|---|---|---|
| EP | 0316834 | 5/1989 |
| EP | 1206928 | 5/2002 |
| EP | 1239810 | 9/2002 |
| EP | 1386599 | 2/2004 |
| EP | 1402875 | 3/2004 |
| FR | 2844448 | 3/2004 |
| FR | 2844800 | 3/2004 |
| JP | 54020996 | 2/1979 |
| JP | 1125314 | 5/1989 |
| JP | 1160907 | 6/1989 |
| JP | 2202941 | 8/1990 |
| JP | 02275814 | 11/1990 |
| JP | 6192594 | 7/1994 |
| JP | 06507426 | 8/1994 |
| JP | H06211620 | 8/1994 |
| JP | 7053326 | 2/1995 |
| JP | 08027393 | 1/1996 |
| JP | 8208418 | 8/1996 |
| JP | 2000247823 | 9/2000 |

(Continued)

OTHER PUBLICATIONS

U.S. Appl. No. 10/049,623, Tanaka.

(Continued)

*Primary Examiner* — Rebecca Anderson
*Assistant Examiner* — Samantha Shterengarts
(74) *Attorney, Agent, or Firm* — Michael Best & Friedrich LLP

(57) ABSTRACT

The invention relates to a method for the preparation of cosmetic compositions having the texture of a cream. Said preparation is made at the time when the composition is used and includes bringing the following elements into contact with each other: (A) a liquid phase; (B) a powder containing a gelling agent for the liquid phase (A); and (C) an active cosmetic ingredient, whereby the elements are brought into contact by adding phase (A) to phase (B), subjecting a solid powder containing phase (B) and phase (A) in an immobilized form to mechanical stress, said mechanical stress releasing phase (A). The invention also relates to compositions which can be used in the above context, especially (1) compositions containing phase (B) (to which phase (A) is added prior to use); and (2) solid compositions comprising phase (B) and phase (A) in an immobilized form (and which are transformed into a cream when they are applied to the skin).

7 Claims, No Drawings

FOREIGN PATENT DOCUMENTS

| | | |
|---|---|---|
| JP | 2000264813 | 9/2000 |
| JP | 2000309506 | 11/2000 |
| JP | 2001158716 | 6/2001 |
| JP | 2001226230 | 8/2001 |
| JP | 2002326904 | 11/2002 |
| JP | 2003012451 | 1/2003 |
| JP | 200381733 | 3/2003 |
| WO | WO 93/17660 | 9/1993 |
| WO | WO 94/14403 | 7/1994 |
| WO | 01/45643 | 6/2001 |
| WO | WO 02/41854 | 5/2002 |
| WO | 02056844 | 7/2002 |
| WO | WO 02/056844 A1 * | 7/2002 |
| WO | WO 03/003990 A1 * | 1/2003 |
| WO | WO 03/078507 | 9/2003 |
| WO | 2004026968 | 4/2004 |
| WO | WO 2004/026263 | 4/2004 |
| WO | WO 2008/018028 | 2/2008 |

OTHER PUBLICATIONS

Colour Index International, C.I. 77288 and C.I. 77289, extracted from http://www.colour-index.org/fingerprint.aspx?cino=715, 1 page, publication date unknown.

Database WPI Section Ch, Week 200267, Derwent Publications Ltd., London, GB; AN 2001-576098 XP002243516 & KR 329214 B (Aekyung Ind. Co. Ltd), Apr. 10, 2002.

Database WPI Section Ch, Week 200206, Derwent Publications Ltd., London, GB; AN 2002-047130 XP002243515 & KR 2001047861 A (Cheil Jedang Co.), Jun. 15, 2001.

Database WPI Section Ch, Week 200260, Derwent Publications Ltd., London, GB; AN 2002-563435 XP002243528 & KR 2002004140 A (Coreana Cosmetics Co. Ltd.), Jan. 16, 2002.

European Parliament and Council Directive 76/768/EEC dated Jul. 27, 1976, 1-128.

Farah, N. et al., "Etude d'une preparation galenique l'emulsion adsorbee seche. Structure physico-chimique et effet sur la liberation d'un principe actif hydrosoluble," STP Pharma (1986) 2(22):1000-1005.

LCW, a Sensient company, "Surface Treated Pigments (and Minerals)" brochure (2002) 1 page.

LCW, a Sensient company, "Coated Pigments" brochure (2004) 6 pages.

Tanaka, T. et al., "Preparation of surface treated pigments with perfluoroalkyl phosphate," 18th International IFSCC Congress poster presentation, Venezia, Italy, Oct. 3-6, 1994, 13 pages.

United States Office Action for U.S. Appl. No. 10/527,949 dated Oct. 23, 2008 (9 pages).

International Search Report for Application No. PCT/FR03/02732 dated Feb. 26, 2004 (2 pages).

International Search Report for Application No. PCT/FR03/02753 dated Mar. 1, 2004 (2 pages).

Parfums Cosmetiques Actualites, "Foundations reveal their secrets", Sep. 2005, pp. 56-62.

United States Patent and Trademark Office, Office Communication dated Apr. 9, 2008 regarding U.S. Appl. No. 10/527,949, 12 pages.

Japanese Patent Office, Office Action regarding Japanese Patent Application No. 2004-537209 corresponding to U.S. Appl. No. 10/527,948, 3 pages.

Japanese Patent Office Action for Application No. 2004-537209 dated Sep. 24, 2009 (6 pages).

United States Office Action for U.S. Appl. No. 10/527,949 dated Apr. 14, 2009 (13 pages).

Japanese Office Action for Application No. 2004-537220 dated Apr. 21, 2009 (2 pages).

* cited by examiner

LOOSE POWDERS TURNING INTO LIQUIDS UNDER COSMETIC APPLICATION

CROSS-REFERENCE TO RELATED APPLICATIONS

This application is a national stage filing under 35 U.S.C. 371 of PCT/FR03/02732, filed Sep. 16, 2003, which claims foreign priority to French Application No. 02/11515, filed Sep. 17, 2002. Priority is hereby claimed to each of these applications, and these applications are incorporated herein by reference in their entirety.

FIELD OF THE INVENTION

This invention relates to methods for preparing cosmetic compositions having the texture of creams, especially those intended for application to the skin. More specifically, this invention concerns compositions that can be stored and shipped in powder form and can be transformed into a composition having the texture of a cream when they are applied.

Thus this invention specifically concerns compositions in powder form that are transformed into compositions with a creamy texture by adding a liquid phase, either aqueous or oily, this liquid phase is able to be added to the powder by a user (a consumer, for example) just prior to use, or this liquid phase being present from the start within the solid composition in immobilized or encapsulated form, with this encapsulated liquid phase then being released under the effect of a mechanical stress, notably the application of the composition to the surface of the skin.

BACKGROUND OF THE INVENTION

Numerous cosmetic compositions having the texture (consistency) of a cream are currently known. They are widely used in the cosmetics industry because of their structure, agreeable feel and their capacity to carry active ingredients.

However, compositions having the consistency of a cream generally can only be obtained by industrial processes. Yet we are currently seeing an increasing tendency for so-called "mobile cosmetics" that are obtained by mixing powders or liquids contained in single-dose units (capsules, small jars, small packets, etc.), with the user mixing the various components just prior to use. These mobile cosmetic compositions often have the advantage of not containing preservatives, making them particularly appropriate for sensitive skin.

BRIEF SUMMARY OF THE INVENTION

The goal of this invention is to provide solid compositions for making mobile cosmetic compositions that allow a user to prepare compositions having the consistency of a cream (that is, having the organoleptic qualities of a cosmetic cream, especially a soft and agreeable touch and a milky appearance) and don't require industrial processes to do so.

In this context, the inventors discovered, in a surprising fashion, that simply adding a liquid phase to a solid powder that contains a gelling agent for a liquid phase (A) and mineral or organic particles (such as mineral oxide particles, for example, with a surface that may or may not be modified, or polymer particles) having surface properties that give them a weak affinity for said liquid phase, generally results quite quickly (even instantly in most cases) in a composition being obtained that has the texture of a cream, without requiring industrial mixing conditions. In an particularly unexpected fashion, the inventors also demonstrated that if the mixture of the liquid phase and the powder is performed under certain specific process conditions, they result in a composition that integrates the liquid phase yet remains in a solid powder state, and that when the solid powder obtained is subjected to a mechanical stress that releases the immobilized phase (A) (notably by applying the powder to the surface of the skin), the solid powder is transformed into a composition having a creamy texture.

On the basis of these discoveries, this invention notably intends, in a general manner, to provide a method allowing cosmetic compositions having the texture of a cream to be prepared extemporaneously that is at the moment these compositions are applied.

In a specific manner, a notable objective of the invention in this context is to provide an instantaneous or at least very quick method for preparing such compositions that is appropriate for a consumer to use to prepare the composition just prior to applying it.

The invention further intends to provide solid compositions that result in a cosmetic composition with a creamy nature when a liquid phase (preferably water) is added.

Another specific goal of the invention is to provide particular cosmetic compositions that can be transported and stored in solid powder form and that are transformed into a composition with a creamy texture when they are applied to the skin.

DETAILED DESCRIPTION OF THE INVENTION

Thus, in to a first aspect, an object of this invention is a process for preparing a cosmetic composition having the texture (consistency) of a cream, made by a user at the moment said cosmetic composition is applied, with this process characteristically comprising a stage (E) consisting of bringing into contact:
 (A) a liquid phase;
 (B) a solid powder that contains:
  (i) a gelling agent for liquid phase (A)
  (ii) mineral or organic particles having surface properties that give them an affinity for liquid phase (A); and
 (C) an active cosmetic ingredient, which is generally present in the liquid phase (A) or the powder (B) or else which is a component, in whole or in part, of the liquid phase (A) or the powder (B).

"Liquid phase" in the sense of this description means a phase of aqueous or oily nature. Alternatively, the liquid phase (A) used in the process in this invention can be a water-in-oil type emulsion (this would then be considered an "oily nature" phase in the sense of this description), or an oil-in-water type (in which case this phase would be considered as an "aqueous nature" phase here).

As a general rule, the gelling agent (i) can be selected from any agent that can gel the liquid phase (A), that is an agent that can increase the viscosity of said phase and transform it into gel form, generally by obtaining a viscosity of at least 800 mPa·s, and preferably at least 1000 mPa·s (advantageously at least 2000 mPa·s). Most often, we prefer that the gelling agent (i) is selected from gelling agents that provide the fastest possible gelling of the liquid phase (A) when said agent and said phase are mixed, preferably instantaneous. Thus, generally, the gelling agent (i) used in the process of this invention causes the viscosity of the liquid phase (A) to be increased by gelling less than 5 minutes after mixing, and advantageously less than 1 minute after mixing. Even more preferentially, the gelling occurs less than 20 seconds after mixing, and especially preferentially less than 10 seconds (or even less than 5 seconds, or advantageously even less) after mixing. It is further preferable, in general, that the gelling agent (i) is able to integrate a significant amount of phase (A).

The mineral oxide particles (ii) in the solid powder (B) are characteristically particles that have surface properties that give them a weak affinity for the liquid phase (A). In other words, the particles (ii) have a hydrophobic surface nature if phase (A) is aqueous, and a hydrophilic surface nature of phase (A) is oily. Thus, when liquid phase (A) is an aqueous phase or an emulsion in which the continuous phase is aqueous, the particles (ii) are generally particles of hydrophobic polymers, mineral particles (metallic oxides, for example), grafted with hydrophobic groups, or else particles on whose surface hydrophobic compounds are deposited (such as oils). When phase (A) is an oily phase, or an emulsion in which the continuous phase is oily, the particles (ii) are advantageously lipophobic particles (for example mineral particles, such as oxides possibly grafted with lipophobic groups, or else mineral or organic particles on whose surface water or an aqueous phase is deposited).

Generally, no matter what their precise nature, the average size of particles (ii) is preferably less than or equal to 5 microns, or preferably less than or equal to 3 microns, with this size typically on the order of several dozen nanometers to several hundred nanometers.

"Active cosmetic ingredient" here means, in a broad sense, any compound or mixture of compounds that can confer a cosmetic character to the composition obtained using the process of the invention, for example by conferring an optical effect to this composition (colorant, lightener, sun block, etc.) or a treatment effect with a cosmetic character (perfume, antiperspirant, moisturizer, slimming agent, etc.). Typically, a cosmetic agent (C) according to the invention can notably be a coloring agent (solid pigment or soluble colorant, for example).

Whatever the nature of the active cosmetic ingredient (C) used in the process of this invention, it can vary widely, notably as a function of the nature of the liquid phase (A) and the solid powder (B) used. Most often this active cosmetic ingredient is either integrated in the solid powder (B) (especially if it is a solid or a liquid that is insoluble in phase (A)), or integrated in the liquid phase (A) (for example if it is an active ingredient soluble in this phase). The active cosmetic ingredient (C) can be made up in whole or in part of the liquid phase (A) or the solid powder (B). In a particular variation, liquid phase (A) and liquid phase (B) can both contain active cosmetic ingredients that can be the same or different.

The process that is the object of this invention is in fact a method that allows a cosmetic composition to be prepared by a user at the time said cosmetic composition is used.

In a first imaginable variation, the method of the invention can consist of simply adding phase (A) to the solid powder (B), or more generally, to a mixture of the two phases (A) and (B). In this case, the process of the invention can notably be implemented by a user in the context of preparing a "mobile" cosmetic composition. In this case, just prior to use, the user adds phase (A) (for example water or an aqueous composition, or an oil that may or may not contain active ingredients) to the powder (B), to end up with a cosmetic composition having the consistency of a cream. In this case, the composition is generally formed instantly or nearly instantly during mixing, that is, most often in less than 30 seconds, and advantageously in less than 5 seconds, unless this produces a less than uniform mixture. This process is thus particularly usable for the instant "mobile" preparation of a cosmetic composition. In this context, phase (A) and the solid (B) can typically be mixed by adding phase (A) to the phase (B) contained in a capsule-type container, with the gelling then generally obtained by simply turning the capsule containing the mixture back and forth two or three times, by which means the composition with the desired creamy texture is obtained. Phase (A) and phase (B) can also, more simply, be mixed in the palm of the user's hand.

In another imaginable variation of the process of the invention, phase (A) can be immobilized on a solid carrier (adsorbed or deposited on this carrier) or encapsulated in a solid carrier, with this solid carrier making up in whole or in part powder (B). Thus, according to this variation, the solid carrier can for example be dispersed within powder (B), or powder (B) in its entirety serves as a carrier for phase (A). In this particular variation, stage (E) of the process of the invention consists of releasing the phase (A) immobilized in the solid carrier, subjecting powder (B) that contains phase (A) in an immobilized form to a mechanical stress (this mechanical stress could, in particular, be performed by applying powder (B) integrating phase (A) to the skin's surface).

In this second variation, powder (B) that contains phase (A) can be considered a solid precursor of the cream composition that will be obtained in the end.

No matter what variation is used, the process of the invention should generally be adjusted for the liquid phase (A) that is used.

Thus, in a first aspect, the phase (A) used in the process of the invention can be an aqueous phase. In this case, this is generally water, an aqueous solution or an oil-in-water type emulsion. This aqueous phase may or may not contain active ingredients.

When phase (A) is an aqueous phase, the gelling agent (i) can especially be selected from among the aqueous phase gelling agents of natural origin that are commonly used in cosmetics, especially those of vegetable origin such as grain, plant, fruit or algae extracts, or from gelling agents of microbial origin such as exocellular derivatives, or from gelling agents of animal origin such as proteins (especially milk), gelatins or chitosanes. These agents could also be of mineral origin, especially clays or amorphous silicon dioxides. They could further be semi-synthetic compounds such as modified celluloses or modified starches, or synthetic compounds such as acrylic or polyacrylamide compounds. In a particularly preferential manner, the gelling agent (i) is a starch, generally cross-linked and preferably modified with carboxymethyl groups, or modified cellulose, agar-agar or an alginate.

Also, and more generally, when phase (A) is aqueous we prefer that gelling agent (i) be such that, when put in an emulsion in the water at 2 weight %, after 5 minutes (advantageously in less than 1 minutes and even more advantageously in less than 10 seconds, and preferably instantly, that is in less than 5 seconds or even less), we obtain a gel with a viscosity at least equal to 800 mPa·s, preferably equal to 1000 mPa·s, and advantageously greater than or equal to 2000 mPa·s.

An especially advantageous gelling agent (i) in the process of the invention, when phase (A) is aqueous, is a cross-linked starch modified with carboxymethyl groups having a molecular weight between 100 and $10^9$ g/mol (advantageously between 500,000 and 100,000,000 g/mol), with this molecular weight preferably being between 5,000,000 and 50,000,000 g/mol, and advantageously between 25,000,000 and 35,000,000 g/mol. A particularly advantageous gelling agent (i) in the process of the invention is the starch modified by carboxymethyl groups with a weight of 30,000,000 g/mol marketed by the LCW Company as "Covagel" (sodium carboxymethyl starch).

More generally, when phase (A) is aqueous, we can use any cross-linked modified starch as the gelling agent (i) (preferably weakly modified by carboxymethyl groups). When the gelling agent (i) is a starch, we prefer that it be such that, when mixed with water at 2 weight %, in at most 10 minutes (advantageously in less than 5 minutes or even in less than 30 seconds) we obtain a gel with a viscosity between 3000 and 6000 mPa·s.

When phase (A) is aqueous, the particles (ii) are generally either particles on whose surface an oily phase is deposited (particles saturated with oil, for example), or hydrophobic polymer particles, or mineral particles (metallic oxides, for example), whose surfaces are grafted (treated) with hydrophobic groups, preferably selected from silane groups or methicone, dimethicone, fatty acid, amino acid, lecithin, polyethylene, Teflon, lauryl lysine groups, fluorinated groups (in particular polyfluorophosphate ethers preferably perfluoroalkyl phosphates), as well as mixtures of one or several groups of this type, especially mixtures of the type polyacrylate/silicone, polyacrylate/lecithin, polyacrylate/fluorinate groups, polyacrylate/silicone/fluorinated groups, or silicone/fluorinated groups, silane groups and fluorinated groups such as polyfluorophosphate ethers being the particularly preferred groups.

In cases where the particles (ii) are mineral particles with their surfaces grafted with hydrophobic groups, we prefer that these particles have a metallic oxide base, and generally a base of silica, titanium dioxide, aluminum, iron oxide or a mixture of these oxides. In a particularly advantageous manner, particles (ii) are particles with a titanium dioxide base comprising, when applicable, usually at least 90 weight %, and preferably at least 95 weight % titanium dioxide. The size of these titanium dioxide-based particles is generally less than or equal to 5 microns, preferably less than or equal to 1 micron, and more advantageously between 20 and 100 nm.

In a particularly advantageous manner, when phase (A) is aqueous, particles (ii) can be particles of oxide, specifically titanium dioxide, grafted with silane groups, with these particles preferentially being particles of titanium dioxide treated with silane of formula $RSi(OR')_3$, where R designates an alkyl group with 5 to 18 carbon atoms, R preferably representing a hexyl, heyptyl, octyl, nonyl, decyl or undecyl radical, and R' representing preferably a methyl, ethyl or propyl group. For the titanium dioxide particles grafted with silane groups than can advantageously be used in this context, we can cite the particles that result from treatment with a trimethoxy caprylyl silane or a triethoxy caprylyl silane.

When phase (A) is aqueous it can be encapsulated in a solid carrier or else immobilized, that is adsorbed or carried on the surface of a solid carrier, this solid carrier being dispersed in powder (B) or a component of powder (B). In this case, stage (E) consists of releasing phase (A) by subjecting powder (B) that contains phase (A) in encapsulated or immobilized form to a mechanical stress, with this mechanical stress possibly in particular being applied when the powder (B) that contains phase (A) is applied to the skin. In this case, the powder (B) that contains phase (A) is a precursor to the cosmetic composition having the texture of a cream that will be obtained after application. Preferably, when phase (A) is aqueous it is immobilized at the surface of the silane-grafted particles, these particles advantageously being particles of titanium dioxide grafted with silane groups as defined previously.

In another variation of the invention, the phase (A) that is used can be oily, notably with an oil of vegetable or animal origin, or synthetic oil, or else a water-in-oil type of emulsion, and this oily phase may or may not comprise an active cosmetic compound.

When phase (A) is oily, the gelling agent (i) can generally be selected from micas (and notably modified micas), silicas (preferably lipophilic), and clays that may or may not be modified. Micas, especially modified micas, and hydrophobic silicas are particularly preferred. In a particularly advantageous manner, the gelling agent (i) is modified mica when phase (A) is oily. As an example, particularly interesting micas are fluorinated micas, notably those fluorinated and modified by potassium, specifically such as the aluminum, fluoromagnesium and potassium silicate (aluminum fluoro magnesium potassium) marketed by LCW as "Submica M."

When phase (A) is oily, particles (ii) can advantageously be mineral particles, and notably oxide particles, preferably made up, in whole or in part, of a titanium dioxide, a silica, and an iron oxide and/or aluminum oxide, with these particles either untreated or treated by grafting lipophobic groups onto their surface. Thus, particles (ii) can advantageously be titanium dioxide particles, preferably grafted with fluorinated groups, with the titanium dioxide particles grafted with fluorinated groups preferably being obtained by grafting with compounds such as perfluoroalkyl silanes, linear or cyclic polyorganosilaxanes containing perfluoroalkyl groups, or perfluoropolyethers, with titanium dioxide-based groups treated with perfluoroalkyl phosphates being particularly preferred. When phase (B) is oily, particles (ii) can alternatively be either mineral or organic particles on whose surfaces water is deposited.

In a more general manner, when phase (B) is oily, it is generally preferred that the size of particles (ii) be less than 5 microns, preferably less than or equal to 1 micron, with this size generally falling between 20 and 100 nm.

In a specific variation, when phase (A) is oily it can be immobilized on (or encapsulated in) a solid carrier, this solid carrier being dispersed in powder (B) or being a component of powder (B). Stage (E) of the process of the invention consists in this specific case or releasing phase (A) by subjecting powder (B) that contains phase (A) in encapsulated or immobilized form to a mechanical stress, this mechanical stress specifically able to be performed by applying powder (B) that contains phase (A) on the surface of the skin. In this case, the powder (B) that contains phase (A) can be considered a precursor of the composition having the consistency of a cream that will be obtained in the end. In this case, the oily phase can notably be encapsulated in microcapsules, or else be adsorbed or deposited on the surface of the particles in solid powder (B). In this case, it is generally preferred that particles (ii) be mineral particles with lipophobic groups grafted onto their surfaces, and advantageously particles made up in whole or in part of a titanium dioxide, a silica, and an iron oxide and/or aluminum oxide treated with fluorinated groups as defined above.

In another aspect, this invention also concerns various solid compositions that can be used in a process of the invention.

Thus, in a particular aspect, this invention concerns solid compositions that very quickly and preferably instantly result in the formation of a composition with the texture of a cream when they are mixed with a liquid phase.

In this context, and in a specific aspect, this invention concerns a composition (C1) that allows a cosmetic composition to be prepared (preferably instantly) upon contact with a liquid phase (A), said composition being made up in whole or in part of a solid powder containing:
  (i) a gelling agent for said liquid phase (A); and
  (ii) particles having surface properties that give them a weak affinity for said liquid phase (A).

In composition (C1), the gelling agent (i) and metallic oxide particles (ii) are preferably selected from the preferred gelling agents and metallic oxide particles defined above, depending on the nature of liquid phase (A) planned.

Thus the invention specifically concerns compositions appropriate for the preparation of cosmetic compounds upon contact with an aqueous phase at the time these compositions are used in which the gelling agent (i) and particles (ii) are as defined early in the specific case in which phase (A) is aqueous. In this context, composition (C1) is advantageously a composition in which the gelling agent (i) is a starch, preferably cross-linked and modified by carboxymethyl groups, with this starch particularly advantageously being a modified starch like "Covagel" marketed by LCW (sodium carboxymethyl starch), particles (ii) preferably being particles with a hydrophobic compound like oil, for example, deposited on their surfaces.

In another aspect, this invention also concerns compositions appropriate for the preparation of cosmetic compounds upon contact with an oily phase at the time said compositions are applied in which the gelling agent (i) and particles (ii) are as defined earlier in the case in which phase (A) is oily. In this context, we prefer that that the gelling agent (i) be a modified mica (advantageously a fluorinated mica, preferably modified with potassium, such as the aluminum fluoro magnesium potassium silicate marketed by LCW as "Submica M").

Composition (C1) in powder form may or may not contain an active cosmetic ingredient.

Specifically, this invention concerns a kit for preparing cosmetic compositions at the time they are applied, comprising (I) a container holding a composition (C1) as defined earlier, and (II) a container holding liquid phase (A), in which the composition in container (I) and/or the liquid phase in container (II) contain an active cosmetic ingredient.

Typically, a composition (C1) according to the invention especially appropriate for use in a kit of the aforementioned type can have the following formula (percents given are weight percents expressed in relation to the total weight of the composition):

| | |
|---|---|
| gelling agent(s) | 0.1-90% |
| particles, with or without treated surfaces | 0.1-60% |
| oil, polar or nonpolar | 0-30% |
| oil emulsifier (modified mica, for example) | 0-10% |
| hydrophilic active ingredient (powder or liquid) | 0-30% |
| lipophilic active ingredient | 0-10% |

In another aspect, this invention also concerns cosmetic compositions (C2) in powder form are transformed into a cream when applied, with these cosmetic compositions made up in whole or in part of a solid powder that contains a liquid phase (A) that is encapsulated or immobilized on the surface of a solid, combined with:
(i) a gelling agent for said liquid phase (A); and
(ii) metallic oxide particles with surface properties giving them a weak affinity for liquid phase (A).

Composition (C2) according to the invention is an extremely particular composition that has the property of being available in the form of a non-wetting solid during transportation and storage and that is transformed into a composition with the agreeable texture and feel of a cream when applied.

Generally, in composition (C2), components (i) and (ii) must of course be adjusted depending on the nature of liquid phase (A). In composition (C2) it is preferred that the gelling agent (i) and the metallic oxide particles (ii) are selected from the preferred gelling agents and metallic oxide particles defined above, depending on the nature of liquid phase (A) planned.

When liquid phase (A) is aqueous, we prefer that this liquid phase (A) be immobilized at least in part at the surface of mineral particles grafted with hydrophobic groups, with these particles preferably having a mineral oxide base (preferably a titanium dioxide base), grafted with silane groups, preferably —OSiR groups in which R designates an alkyl group with 5 to 18 carbon atoms, and preferably between 7 and 10 carbon atoms (typically 8 carbon atoms), or with fluorinated groups such as perfluoroalkyl phosphates.

When phase (A) is aqueous, we prefer that the gelling agent (i) be a starch, preferably cross-linked and modified with carboxymethyl groups, with this starch preferably being one like the "Covagel" starch marketed by LCW. In this case it is further preferred that particles (ii) have a titanium dioxide base grafted with silane groups (preferably —OSIR groups in which R designates an alkyl group with 5 to 18 carbon atoms, preferably between 7 and 10 carbon atoms and typically 8 carbon atoms) as defined above, the aqueous phase then generally being adsorbed at least partially at the surface of these particles. Without wishing to be linked in any way to a particular theory, it can be suggested in this context that, especially in the case of a composition (C2) in which phase (A) is aqueous, gelling agent (i) is a modified starch, and particles (ii) have a grafted titanium dioxide base, the water appears to be immobilized both at the surface of particles (i) [sic] and in the gelling agent at the same time.

In another variation, composition (C2) can contain a liquid phase (A) that is oily in nature, said oily phase (A) then generally being at least partially immobilized at the surface of the mineral particles (ii) whose surface is grafted with lipophobic groups, these particles being advantageously made up in whole or in part by a titanium dioxide, a silica, and an iron oxide and/or aluminum oxide, preferably graft-treated with compounds such as perfluoroalkyl silanes, polyhexafluoro (propylene oxide), by linear or cyclic polyorganosiloxanes containing perfluoro alkyl groups, by perfluoropolyethers, with titanium dioxide-based particles treated with perfluoroalkyl phosphates being especially preferred. In this variation, it is most advantageous for the gelling agent (i) to be made up, in whole or in part, of particles of modified mica, preferably particles of fluorinated mica (in particular the type of particles marketed as "Submica M" by LCW).

No matter what the exact formulation or nature of immobilized phase (A) is, a composition of the (C2) type as defined above is generally obtained by adding liquid phase (A) (usually at once and quickly) to a solid mixture containing gelling agent (i) and particles (ii), generally under moderate stirring (typically between 1000 and 2000 rotations per minute).

In a particular aspect, this invention further concerns cosmetic compositions in powder form that result from the mixture of two or more compositions of the (C2) type as defined earlier. In this variation, one could for example imagine compositions resulting from at least one (C2)-type composition in which phase (A) is aqueous and at least one (C2)-type composition in which phase (A) is oily.

Typically, a (C2) composition according to the invention can have the following formula (percents given are weight percents expressed in relation to the total weight of the composition):

Solid Phase:

| | |
|---|---|
| gelling agent(s) | 0.1-15% |
| particles, with or without treated surfaces | 0.1-30% |
| hydrophilic or lipophilic active ingredient | 0-30% |

Liquid Phase Immobilized within the Solid Phase:

| | |
|---|---|
| oil or water, polar or non polar | 10-90% |
| oil emulsifier (modified mica, for example) | 0-10% |
| hydrophilic or lipophilic active ingredient | 0-30% |

As emphasized earlier, the processes of this invention, as well as compositions (C1) and (C2) that use them, can advantageously include a modified starch such as "Covagel" as the gelling agent for the aqueous phase.

In terms of starches, the inventors demonstrated, in a surprising manner, that although these modified starches are generally known as being inappropriate in cosmetics because they are not conducive to lasting gelling properties, cross-linked and carboxymethyl starches like "Covagel" can be used advantageously in cosmetics as gelling agents, in the context of preparing mobile cosmetic compositions and in the context of the particular (C2) cosmetic compositions that are in powder form and are transformed into a cream when applied. In fact, the inventors demonstrated that modified starches, and in particular cross-linked and carboxymethyl starches like "Covagel", instantly provide a composition with the soft, agreeable texture of a cream when water is added, and that because of this these starches allow water-based cosmetic compositions with particularly interesting qualities of touch to be obtained quite quickly.

A further specific object of this invention is this particular use of modified starches like the "Covagel"-type starches to prepare water-based cosmetic compositions at the time they are applied.

In the same manner, the inventors demonstrated that modified mica particles, particularly fluorinated mica particles, and particularly fluorinated mica particles modified with potassium like those marked as "Submica M" by LCW, instantly provide a composition with the agreeable texture of a cream when an oil phase is added, and that these mica particles are therefore particularly appropriate for instant preparations to very quickly obtain oil-based cosmetic compositions with an especially agreeable feel.

A further specific object of the invention is this specific use of modified mica particles (particularly fluorinated) like "Submica M" for the extemporaneous preparation of cosmetic compositions with an oil phase base at the time they are applied.

Various characteristics and advantages of this invention will appear even more clearly with the illustrative examples given below.

Example 1

Composition in Powder Form that is Instantly Transformed into a Composition with the Texture of a Cream by Adding Water (Day Cream)

We prepared a composition (C1) according to the invention by mixing the following compounds (percents given are weight percents expressed in relation to the total weight of the composition):

| | |
|---|---|
| Covagel* (sodium carboxymethyl starch - M = 30.10$^6$ g/mole) | 30% |
| Submica M* (aluminum, fluoromagnesium and potassium silicate) | 5% |
| Covabead LH 85* (cross-linked polymethylmetacrylate) | 30.5% |
| AC-5 sericite FSE* (aluminum and potassium silicate, cellulose) | 10% |
| Fucosorb* (algae extract) | 10% |
| LRI solubilizer* (PPG-26 buteth-26, PEG-40, hydrogenated ricin oil) | 2.5% |
| Macarose* (Macadamia Ternifolia, Rosa canina) | 10% |
| Lipofacteur vitentiel* (Rosa canina, tocopheryl acetate, retinyl palmitate, liquid paraffin, ascorbyl palmitate) | 2.0% |

*Marketed by LCW

This can be used as a "mobile" cosmetic composition. Just before use, one must merely hydrate the formulation by adding water and shaking the powder/water mixture lightly, and one obtains a structure with a creamy texture and appearance and a particularly agreeable feel.

Example 2

Solid Powder that is Instantly Transformed into a Cream when Applied (Slimming Cream Containing an Immobilized Aqueous Phase)

The compounds used in this example and their proportions are given below. The percents given are weight percents expressed in relation to the total weight of the final composition.

Solid Powder:

| | |
|---|---|
| Covagel* (sodium carboxymethyl starch – M = 30.10$^6$ g/mole) | 3.8% |
| Serica 5 covasil 4.05* (mica + silicone) | 2.4% |
| Talc covasil 4.05* (talc + silicone) | 3.3% |
| PF-5 talc JA 46R* (talc treated with perfluoroalkyl phosphates) | 3.8% |
| Covabead LH 85* (beads of cross-linked methylmetacrylate) | 2.4% |
| PW covasil S1 (titanium dioxide treated with trimethoxy caprylyl silanes) | 3.3% |

Aqueous Liquid Phase:

| | |
|---|---|
| Water | 65.7% |
| Lipofirm LCW* (slimming active ingredients) | 7.5% |
| Fucosorb* (algae extract) | 1.9% |
| PEG 400 | 5.6% |
| Preservatives | 0.3% |

*Marketed by LCW

We added the liquid phase to the solid powder all at once and left the mixture stirring at 1500 rpm for 10 minutes. We first obtained a gel structure, friable, that progressively broke apart to be progressively transformed into a composition with the structure of a powder.

The powder obtained can be stored in that state and transported, and will take on an agreeable feeling creamy texture when applied to the skin.

Example 3

Solid Powder that is Instantly Transformed into a Cream when Applied (Composition Containing an Immobilized Oil Phase)

We prepared a mixture of 15 g of PW Covafluor (titanium dioxide grafted with fluorinated groups, marketed by LCW), 5 g of talc JA R46 PF (talc treated with fluorinated groups, marketed by LCW), 5 g of Submica M, and 2 g of Covabead LH 170 (beads of polymethacrylate, marketed by LCW). We added 30 g of Squatol S (hydrogenated polyisobuten, marketed by LCW) to this mixture all at once.

The oily hydrogenated polyisobuten was integrated into the powder during stirring (1500 rpm for 10 minutes), and at the end we obtained a solid powder that can be transported and stored in solid form and that takes on the texture of a cream when it is applied to the skin.

The invention claimed is:

1. A cosmetic composition comprising:
   an aqueous liquid phase; and
   a powder, the powder comprising:
      a gelling agent for the liquid phase; and
      mineral or organic particles having a hydrophobic surface nature,
   wherein the liquid phase is encapsulated in or immobilized on the surface of a solid carrier, the solid carrier being dispersed in the powder or a component of the powder,
   and wherein the cosmetic composition is in a powder form that is transformed into a cream upon application.

2. The cosmetic composition of claim 1, wherein the gelling agent comprises a starch modified by carboxymethyl groups, and the mineral particles comprise titanium dioxide-based particles treated with a silane group, a fluorinated group, or a combination thereof.

3. The cosmetic composition of claim 2, wherein the cosmetic composition is transformed from a powder form into a water-based composition with the texture of a cream upon application.

4. A cosmetic composition comprising:
   an oil-based liquid phase; and
   a powder, the powder comprising:
      a gelling agent for the liquid phase; and
      mineral or organic particles having a lipophobic surface nature,
   wherein the liquid phase is encapsulated in or immobilized on the surface of a solid carrier, the solid carrier being dispersed in the powder or a component of the powder,
   and wherein the cosmetic composition is in a powder form that is transformed into a cream upon application.

5. The cosmetic composition of claim 4, wherein the gelling agent is made up in whole or in part of particles of modified mica, and the mineral particles comprise metallic oxide particles with lipophobic groups grafted on their surface.

6. The cosmetic composition of claim 5, wherein the gelling agent comprises fluorinated mica particles, and wherein the cosmetic composition is transformed from a powder form into an oil-based composition with the texture of a cream upon application.

7. The cosmetic composition of claim 6, wherein the mica particles are fluorinated and modified with potassium.

* * * * *